United States Patent
Sharma

(10) Patent No.: US 12,227,728 B2
(45) Date of Patent: Feb. 18, 2025

(54) SURFACE MODIFIED SEPARATION MEDIA

(71) Applicant: Applied Membrane Technology, Inc., Minnetonka, MN (US)

(72) Inventor: Ashok Sharma, Hopkins, MN (US)

(73) Assignee: Applied Membrane Technology, Inc., Minnetonka, MN (US)

( * ) Notice: Subject to any disclaimer, the term of this patent is extended or adjusted under 35 U.S.C. 154(b) by 840 days.

(21) Appl. No.: 17/158,651

(22) Filed: Jan. 26, 2021

(65) Prior Publication Data

US 2022/0235306 A1    Jul. 28, 2022

(51) Int. Cl.
| C12M 1/12 | (2006.01) |
| B01D 67/00 | (2006.01) |
| B01D 69/02 | (2006.01) |
| B01D 71/28 | (2006.01) |
| B05D 3/14 | (2006.01) |
| B05D 5/00 | (2006.01) |
| B05D 7/04 | (2006.01) |
| C09D 165/04 | (2006.01) |

(52) U.S. Cl.
CPC ......... C12M 25/02 (2013.01); B01D 67/0002 (2013.01); B01D 67/009 (2013.01); B01D 69/02 (2013.01); B01D 71/28 (2013.01); B05D 3/148 (2013.01); B05D 5/00 (2013.01); B05D 7/04 (2013.01); C09D 165/04 (2013.01); B01D 2323/02 (2013.01); B01D 2323/04 (2013.01); B01D 2323/10 (2013.01); B01D 2323/35 (2013.01); B01D 2323/46 (2013.01); B01D 2325/36 (2013.01); B01D 2325/38 (2013.01)

(58) Field of Classification Search
None
See application file for complete search history.

(56) References Cited

U.S. PATENT DOCUMENTS

| 4,500,562 A | 2/1985 | Jahn et al. |
| 5,643,580 A * | 7/1997 | Subramaniam ..... A61L 33/0076 427/535 |
| 6,159,531 A * | 12/2000 | Dang .......... C08J 7/12 427/2.24 |
| 6,521,012 B2 | 2/2003 | Lamon et al. |
| 9,834,459 B2 | 12/2017 | Tuteja et al. |
| 9,868,911 B2 | 1/2018 | Reams et al. |
| 10,722,847 B2 | 7/2020 | Lin et al. |
| 2002/0189455 A1* | 12/2002 | Lamon ............... D06M 15/233 96/12 |
| 2011/0236745 A1 | 9/2011 | Brant et al. |
| 2016/0032069 A1 | 2/2016 | Kim et al. |
| 2016/0226023 A1 | 8/2016 | Chen et al. |
| 2020/0129975 A1 | 4/2020 | Park et al. |

FOREIGN PATENT DOCUMENTS

| CN | 106110762 A | 11/2016 |
| WO | 2020018925 | 1/2020 |

OTHER PUBLICATIONS

Golda-Cepa et al. "Recent progress on parylene C polymer for biomedical applications: A review." Progress in Organic Coatings 140 (2020) 105493, pp. 1-16. (Year: 2020).*
Pall Corporation, "Material Selection for Venting Applications", Mar. 2012, 8 pages.
International Search Report and Written Opinion issued on Apr. 1, 2022 in International Application Serial No. PCT/US2022/012293.
"Communication pursuant to Rules 70(2) and 70a(2) EPC mailed on Dec. 6, 2024", 3 pages.
"Supplement European Search Report mailed on Dec. 10, 2024", 2 Pages.

* cited by examiner

*Primary Examiner* — William H. Beisner

(74) *Attorney, Agent, or Firm* — Billion & Armitage

(57) ABSTRACT

A substrate surface may be modified with a polymer coating to render the surface suitable for plasma functionalization. The polymer coating is deposited onto the surface at ambient temperature to a thickness of less than 0.1 μm. The polymer coating includes poly(p-xylylene) or a derivative thereof, and is capable of penetrating into pores of a porous substrate while no substantially altering the porosity of the substrate. The coated substrate is selected from a material lacking a primary or secondary aliphatic hydrogen atom.

15 Claims, No Drawings

SURFACE MODIFIED SEPARATION MEDIA

FIELD OF THE INVENTION

The present invention relates to surface treated substrates generally, and more particularly to modification of substrate surfaces to promote cellular growth and separation efficiency through enhanced functionality, biocompatibility, bondability, hydrophilicity, hydrophobicity and/or oleophobicity.

BACKGROUND

Commercially available membranes are typically hydrophobic and are often fabricated from polyethylene (PE), polypropylene (PP), polymethylpentene (PMP) polytetrafluoroethylene (PTFE), or other such polymers or copolymers. These membranes often need surface modification to make them hydrophilic and/or functionally active for biomedical and chemical applications. Membranes based on polysulfone (PS), polyethersulfone (PES), and polyvinylidinefluoride (PVDF) can be both hydrophobic and hydrophilic but they too lack functionally active sites and may suffer from poor chemical resistance. Membranes based on polybenzimidazole (PBI) or naturally regenerated polymers such as cellulose nitrate and acetate are generally hydrophobic, but require cumbersome membrane casting processes. Ceramic membranes are generally hydrophilic due to their metal oxide content, but lack functionally active groups which can be essential for biological and chemical applications. Thus, finding a functionally active and chemically and physically stable membrane has always been a challenge.

Several biomedical engineering applications involving cellular growth or tissue culture require a surface that can offer a three dimensional topography to better interact with cells and protein to augment their growth and/or provide nutrients or extract product or byproduct and enhance the yield. Hydrophobic polymer membranes (or other membranes lacking compatible functionality) can offer chemically stable structures, but do not always promote cell adhesion and proliferation and hence are not useful unless their surfaces are further modified without affecting their bulk properties. The biocompatibility and sterilizability of such surfaces may also pose limitations. For example, PTFE porous membranes may lack dimensional stability at high temperatures and may degrade upon exposure to gamma sterilization.

Plasma treatment has now been recognized as a versatile technique for surface modification and is commercially used for creating biocompatible, bio-inert, bio-functional and lubricious surfaces. The process may take place at room temperature under reduced pressure conditions and without solvents. Plasma polymerization techniques are very useful for depositing ultrathin coatings that are crosslinked and thermally and chemically stable. Both organic and inorganic compounds can be plasma polymerized with equal ease and even nonfunctional organic compounds such as methane, tetramethyldisiloxane, perfluoroalkanes, and the like can be successfully polymerized to produce useful coatings. Plasma treatment with inorganic compounds is often used for surface treatments and surface functionalization. Copolymers that combine the properties of individual monomers can be prepared with myriad of properties by polymerizing blends of functionally and structurally different chemical compounds. An example is fluoro-silicone copolymers that can be produced by combining fluoro- and silicone compounds in plasma polymerization. It is even possible to deposit metal coatings or incorporate metals in polymer matrix by the plasma treatment of organometallic compounds.

The coatings produced by plasma polymerization are generally less than 0.5 μm in thickness and very often less than 0.1 μm in thickness. At such thicknesses, the bulk properties of the underlying substrate are typically not affected. This is especially useful in biomedical applications where engineers are often forced to work with tight dimensions and limited number of useful polymers. Many commercial applications of plasma polymerization have been developed in the past 25 years. One such application that involves deposition of a thin lubricious Polysiloxane coating on pacemaker and defibrillator leads has been in commercial use for over 20 years.

Plasma treatment with non-polymer forming gases such as argon, oxygen, nitrogen, ammonia, carbon dioxide, and sulfur dioxide lead to surface modifications that often yield hydrophilic surfaces. This kind of treatment is generally limited to the top few atomic layers of the substrate surface. Plasma treatment with non-polymer forming gases is often used for improving bondability of the surface and more recently for the chemical functionalization of the substrates for accelerating biochemical processes. The amino, oxy, hydroxyl, hydroperoxy, sulphonic, and carboxy-functionalities produced by non-polymer forming gas treatment offer enhanced interaction with biological molecules making the membranes useful for biosynthesis and bioseparation.

It is imperative, however, that the substrate membrane be able to withstand the highly energized environment of plasma treatment. Generally, solid polymeric substrates such as polyalkenes (PE, PP, PMP), PTFE, PEEK, and PBI and ceramics are mechanically, thermally and chemically strong, energy stable, and are not significantly affected by the energetic plasma environment. Highly porous substrates such as expanded polytetrafluorothylene (ePTFE) and other ultrathin microporous membranes, however, can be easily damaged in a plasma treatment process. The activated ions, radicals, energized electrons and photons that comprise plasma can often degrade these substrates even under the mildest plasma conditions. The degradation is often revealed in the shrinkage of the substrate, loss of or damage to porosity and sometimes the complete destruction of the substrate's mechanical properties. There is thus a need for a process that can be used to modify surfaces of sensitive substrates for plasma functionalization. In addition, it is noted that the fibril structure of pores in a porous membrane is often prone to attack by heat and chemicals, even though the bulk polymer itself may be resistant to attack. The chemical attack may lead to swelling of the membrane, which alters its pore size and morphology and in some instance degrades the polymer network itself. There is thus a need to enhance the chemical integrity of porous membranes for use in applications involving harsh organic and inorganic solvents.

In some applications involving membrane distillation, there is a need to reduce the break through pressure also called liquid entry pressure (LEP) of the membrane surface in contact with the distillate in order to facilitate water vapor transport across the membrane. While some polymeric membranes such as polyethylene and polypropylene membranes are easier to modify (for example aminate or oxidize) by plasma treatment due to the availability of primary or secondary aliphatic hydrogen atoms in the structure, other polymers such as PTFE and PEEK do not have such functionalities in their structure and are hence difficult to functionalize by plasma treatment. There is thus a need for a technique that can functionalize such substrates without affecting their physico-mechanical properties.

Ceramic membranes often times comprise inorganic materials such as alumina, zirconia, titania, and silicon carbide. These membranes offer superior mechanical, thermal and chemical properties and can be used in harsh environments. They are generally hydrophilic and water wettable due to the high surface energy of inorganic salts, and are extensively recommended for water filtration applications. However, many ceramic membranes are prone to fouling due to pore wetting and can clog during application requiring high maintenance. In addition, these membranes lack reactive functionality such as amino, sulfo, or halo groups in the membrane structure. The lack of functionality prevents chemical attachment of biological molecules such as heparin to their surface, and as a result limits the use of ceramic substrates in biomedical applications. Plasma treatment offers a convenient means for modifying the surface hydrophobicity of such substrates, but is inadequate to alone provide functional activity.

SUMMARY OF THE INVENTION

The present invention provides a surface-modified composite structure comprising a substrate and a polymer coating on at least one surface of the substrate. The surface modification may enhance mechanical and/or chemical properties of the substrate, and may also or instead facilitate plasma functionalization of substrates which are otherwise unsuitable for plasma treatment.

The surface modification includes the deposition of a shield in the form of a thin polymer layer on the substrate that conformally coats and strengthens the fibril structure of the membrane without substantially altering its porosity. The thin conformal coating has a thickness of less than 0.1 μm and provides the necessary chemical structure to render the substrate surface suitable for plasma functionalization. In this manner, the coating may act as an intermediate layer in which neither the chemical nor the physico-mechanical and thermal integrity or the porosity of the substrate is compromised. The process of this invention may improve the tensile properties of the substrate, and provide a base structure receptive to plasma treatment or deposition. In some embodiments, the polymer layer may be deposited under reduced pressure at ambient temperature without involvement of solvent and in the same apparatus that supports a subsequent plasma treatment. The intermediate layer/polymer coating may comprise Poly(p-Xylylene) or a derivative thereof.

A method for modifying a surface of a porous substrate includes depositing a polymer onto the surface at ambient temperature to a thickness of less than 0.1 μm, wherein the polymer includes poly(p-xylene), also referred to as Parylene, or a derivative thereof, and wherein the polymer penetrates into pores of the porous substrate without significantly altering its porosity. The porous substrate is selected from one or more materials which lack a primary or secondary aliphatic hydrogen atom, with the polymer coated surface being rendered suitable for plasma functionalization.

In some embodiments, the method further includes chemically bonding a functional agent to the polymer coating, wherein the functional agent is deposited by plasma treatment. The functional agent may be selected from one or more of the group of nitrogen, phosphorous, oxygen, sulfur, fluorine, bromine, chlorine, and iodine.

A composite substrate of the present invention includes a porous body having first and second opposed surfaces and lacking a primary or secondary aliphatic hydrogen. The composite substrate further includes a polymer treatment on at least one of the first and second surfaces, wherein the polymer treatment includes poly(p-xylylene) or a derivative thereof, and has a thickness of less than 0.1 μm. A functional agent is chemically bonded to the polymer treatment by plasma functionalization.

DETAILED DESCRIPTION OF THE INVENTION

It has been discovered that treatment of fragile porous substrates with an thin coating of poly(p-xylylene) polymer can significantly improve not only the mechanical and chemical properties of the substrate, but also the substrate's durability in a plasma energy field, thereby permitting the use of plasma treatment for surface functionalization of the coated substrate. Without treatment, many otherwise useful substrates are susceptible to damage by exposure to even very low plasma energy. Surprisingly, the process of coating of the substrate with Parylene, in spite of its similarity to plasma treatment, has no detrimental effect on the mechanical integrity of the substrate. In fact, deposition of Parylene marginally improves the physico-mechanical and chemical properties of the underlying substrate. Parylene films are known to have excellent mechanical, thermal, and chemical resistance properties often comparable to PTFE polymer.

While typical plasma treatments may produce highly energetic ions and radicals, high temperature electrons, photons and UV energy, the active species formed in the Parylene deposition process lose most of their kinetic energy as soon as they leave the decomposition furnace and enter the deposition chamber where the deposition occurs at room temperature. The Parylene deposition process does not produce the energetic electrons, photons and UV energy that can cause damage to certain fragile substrates that are otherwise useful in a myriad of applications.

The Parylene treatment process of the present invention produces small molecular size active species that are capable of penetration into the pores of porous substrates before propagation on the surface. This results in coating of the fibril structure of the substrate from all directions, resulting in a conformal coating that strongly bonds to the surface of the substrate.

It has been found that a thin layer of Parylene polymer may improve the mechanical properties of the substrate membrane, and offers a protective "shield" for subsequent plasma treatment through which a functional agent may be chemically bonded to the Parylene intermediate. The Parylene coating also provides a chemical structure that facilitates functionalization by plasma treatment, which can be particularly beneficial for imparting functional groups to substrates that lack surface modification sites in their base structures. This is true of substrates that lack a primary or secondary aliphatic hydrogen, such as polytetrafluoroethylene (PTFE) and polyetheretherketone (PEEK) and other such materials.

The substrate of the present invention may be used as a support or a functional body, such as in the instance of a separation membrane, and may be prepared from a suitable material. A polymer material may be a homopolymer, copolymer, terpolymer, or more complex polymer. The polymer may be pre or post treated, and may be combined with one or more additional polymers in the formation process. The porous substrate may be provided in any suitable shape or form, including a film, beads, hollow fibers, and the like, and may be formed through conventional means including casting, extruding, and sedimentation. Substrates include hollow fiber media, melt blown or other nonwoven media, and woven media. Porous films may be symmetrical or asymmetrical as described further below.

In some embodiments, a porous substrate of the present invention may be selected from one or more materials lacking a primary or secondary aliphatic hydrogen. Examples of such materials include polytetrafluoroethylene (PTFE), expanded polytetrafluoroethylene (ePTFE), polyetheretherketone (PEEK), polyvinylidene fluoride (PVDF), and ceramics. Although such materials find wide applicability in separations technologies, they are not typically functionalized with functional agents due to a lack of available binding sites. The process of the present invention renders such materials suitable for functionalization through an intermediate Parylene layer.

The one or more materials lacking a primary or secondary aliphatic hydrogen may be present at less than all surfaces of the substrate. In some embodiments, the one or more materials lacking a primary or secondary aliphatic hydrogen may be present at only a single surface, or a portion of a single surface of the substrate. Surfaces of the substrate may be formed from one or more polymers, one or more polymer isomers, or one or more non-polymer materials.

The substrates suitable for the present invention may include membranes with a symmetric or asymmetric pore structure. For the purposes hereof, the term "asymmetric" refers to a membrane having a pore size gradient or having a variation in pore size. In an example, an asymmetric membrane may have a pore size gradient through its thickness, with average or maximum pore size changing with dimension from a boundary. The pore size of an asymmetric membrane may increase or decrease linearly or non-linearly through the thickness of the membrane. A "symmetric" membrane may exhibit a consistent pore size or pore size distribution through its thickness.

Porous substrates of the present invention may have pore sizes and pore size distributions that are appropriate for the given application. Typical pore sizes may be between 0.001 and 1000 μm. In some embodiments, the porous substrate has a maximum pore size of less than 100 μm. In some embodiments, the porous substrate has a maximum pore size of less than 1 μm. In some embodiments, the porous substrate has a maximum pore size of less than 100 nm.

For the purposes hereof, the term "porosity" means the measure of the void spaces in a material, determined as the volume of voids per total volume. The porosity of a substrate is "not substantially altered" or "not significantly altered" if the porosity or the gas permeability is changed by less than 20%, preferably less than 10%, and more preferably less than 5%.

The substrates may be fabricated from one or more polymers which exhibit hydrophobicity, oleophobicity, or both hydrophobicity and oleophobicity. In other embodiments, the substrates may exhibit hydrophilicity, oleophilicity, or both hydrophilicity and oleophilicity. Substrates of the present invention may have multiple surfaces that exhibit identical, similar, and/or different affinities. The substrate surfaces may be modified to exhibit identical, similar, and/or different affinities. Deposition of Parylene on a substrate surface may at least partially modify its affinity, due to the affinity exhibited by the Parylene at the surface.

A surface of the substrate is preferably modified by depositing a thin polymer coating thereupon. As described above, depositing a thin coating of Parylene, or a derivative thereof, onto a surface of the substrate can enhance the chemical and mechanical properties of the substrate itself, and can also serve as an intermediate material or layer to which another material, such as a functional agent, may be applied. The chloro-, dichloro-, and fluoro-derivatives of poly(p-xylylene) are example derivatives useful in improving the chemical and physico-mechanical properties of the substrate.

The coating material may be derived from one or more para-xylene dimers, which may be converted to a gaseous monomer that condenses and polymerizes on substrates at ambient temperatures. The Parylene coating thickness may be controlled so that the polymer penetrates into pores of a porous substrate, but does not substantially alter porosity of the porous substrate. The Parylene coating may be substantially uniform over the external surface or surfaces of the substrate, and held to a thickness of less than 0.1 μm. In some embodiments, the Paralyne coating thickness is less than 0.05 μm. In some embodiments, the Parylene coating is less than 0.01 μm. In some embodiments, the Parylene coating is less than 0.001 μm.

In preferred embodiments, a single type of Parylene may be deposited in a coating. In other embodiments, a mixture of two or more types of Parylene may be deposited in a coating, either as a mixed chemistry coating layer, or as multiple coating layers each having a distinct Parylene chemistry. The Parylene deposition may be controlled so as to only partially coat the substrate. For example, a Parylene coating may be applied on a membrane on one surface only in a layer not fully penentrating the pores through the entire thickness of the membrane. The Parylene layer may also be deposited in select geometries on the substrate that result in coated and uncoated areas of the substrate surface.

An example Parylene deposition apparatus includes a sublimation furnace, a decomposition furnace which houses a decomposition tube, a deposition chamber, a cold finger to capture the unused monomer, and vacuum pumps. Both the sublimation and decomposition tubes are electrically heated by the two separate furnaces. The deposition chamber is a cylindrical glass bell jar which is in turn connected to a cold finger and subsequently to a vacuum system. The substrates are held in the deposition chamber at room temperature and moved to ensure uniformity of coating, if necessary. p-Xylylene dimer or a derivative (used as Parylene precursor) is placed in the sublimation chamber and the system is evacuated to a pressure of less than 100 mtorr, and preferably less than 50 mtorr. The decomposition tube is heated to 650-700° C. and once the temperature is attained, the sublimation tube is heated to a temperature of 120-180° C., depending on the dimer used to start the deposition process. The thickness of the Parylene coating on the substrate is monitored with an Inficon thickness monitor and the deposition process is arrested by turning off the sublimation furnace and subsequently the decomposition furnace. An inert gas is used to assist the Parylene deposition process in some instances. The coated substrates are then subjected to plasma treatment.

Plasma treatment is a low temperature dry process that also is carried out under vacuum conditions using an electrical discharge operated at, for example, 13.56 MHz. The plasma treatment can be carried out either in the deposition apparatus described above, or in a separate plasma apparatus. Since no solvents are involved, a variety of substrate membranes can be used as long as they can withstand the plasma conditions. The chemical precursor, often called monomer, that leads to plasma process is fed in vapor or gaseous form using a mass flow controller from a reservoir placed outside the plasma apparatus. Both inorganic and organic compounds can be used, with the former preferred for treatment applications and the later for depositing an ultrathin coating of the plasma polymer. Once the system has reached the desired pressure, monomer is fed and the discharge is turned on. Active species, comprising radicals, ions, electrons, photons are formed by the decomposition of the monomer under the influence of RF power, which simultaneously activates and deposits or derivatizes the substrate surface forming strong covalent bonds. The extent of decomposition of the monomer depends on plasma conditions. The deposition process occurs at ambient temperature and the nature of coating obtained, including its thickness, depends on the plasma conditions. Temperature sensitive substrates can be coated/treated so long as they can withstand the plasma energy conditions.

In an aspect of the present invention, the polymer-coated substrate has been found to be a useful composite structure for functionalization. In particular, a functional agent may be bonded to the polymer coating to achieve a desired chemical affinity for the composite structure. An example functionalization is to alter the hydrophobicity of a fragile substrate, such as e-PTFE. Untreated, an e-PTFE substrate is typically hydrophobic. However, many useful applications of e-PTFE may be realized if a surface thereof could be rendered hydrophilic, or at least less hydrophobic. In this example, a Parylene coating may be applied as described herein to a surface of an e-PTFE substrate. Thereafter, a hydrophilic functional agent, such as amine, may be chemically bonded to the Parylene coating with a plasma functionalization process so that the composite structure possesses hydrophilic sites that can be derivatized further if necessary.

A variety of functional agents are contemplated by the present invention, to facilitate a variety of applications for the composite structure. The functional agent may be applied to the coated substrate to create a desired three-dimensional surface topography that interacts with certain species such as blood cells. In other embodiments, the functional agent may be applied to the coated substrate to provide a desired chemical affinity. In still further embodiments, the functional agent may be a metal coating applied to provide certain electrical properties or catalytic activity. Example functional agents include atoms of or molecules containing nitrogen, phosphorous, oxygen, sulfur, fluorine, bromine, chlorine, and iodine.

The functional agent may be applied to the coated substrate through various plasma treatment, as described herein.

Ammonia plasma treated films of this invention, for example, retain a low contact angle with water for extended time periods and exhibit improved mechanical properties. Plasma functionalized film of this invention also offers a convenient mechanism for the covalent attachment of biomolecules such as HPEO, Albumin and Heparin to the coated substrate surface. This in turn enhances the yield of other biomolecules of functional importance, such as the protein growth factor TGF β3. The plasma functionalized coatings of this invention may significantly enhance the growth of cells when incorporated into an implanted device such as a bile stent.

The modified structures of this invention also offer a convenient mechanism for fluorinating the surface of the fragile porous substrates for enhancement of moisture and chemical resistance in biological environments. For example, polybenzimidazole (PBI) and ceramic membranes may be fluorinated to enhance utility in an aqueous environment, or functionalized for attachment of other biological molecules such as heparin. An oxygen plasma treatment of porous substrates prepared as per this invention offered a means of creating oxy-functionalities on the surface of the membrane by plasma oxidation, which can be further functionalized to suit to specific requirements. The surfaces may also be plasma metallized for application in bio-catalysis.

Thus, the modified substrate surfaces of this invention can serve several important functions. The primary polymer coating not only acts as a "shield" toward plasma energy, but may also improve the mechanical properties of the underlying substrate, making it more handleable without any significant alteration in its porosity or chemical resistance. The improvement in mechanical properties is very useful in, for example, biomedical microporous ePTFE type membranes. It can also be beneficially used to modify microporous poly(propylene) films that are used as battery separators or to modify PEEK membranes for water filtration applications.

In some instances the polymeric coating of this invention can significantly improve the chemical resistance of the substrate to chemical degradation and swelling. This is true of substrates made from Polysulfones, Polysiloxanes, Polyurethanes, Polyhydrocarbons, Polycarbonates and others. All these polymers have poor chemical resistance that can be significantly improved by the Parylene treatment of the present invention.

These are just few benefits of this invention that can be commercially exploited. There could be many other advantages, which are known to those knowledgeable in the field of material science, of the novel concept that involves shielding of the substrate structure by a conformal coating which makes the substrate tenable for further modification using plasma surface modification techniques. One such application involves modification of PTFE, PEEK and PVDF membranes to preferentially generate a hydrophilic surface on one side of the membrane while the other side retains its hydrophobic character and the substrate its base porosity. Such membranes are very useful for membrane distillation and solvent-based extraction.

Although the poly(p-xylylene) polymer, or a derivative thereof, is a preferred candidate for generating the shield layer of this invention, due to its chemical inertness, excellent physico-mechanical properties and controllability of thickness, other polymers may also be useful in this endeavor. For example, in certain cases, the polymeric layer may be deposited by a liquid process wherein the polymer is dissolved in a solvent or solvent blend and applied to the substrate by dip, spray or roller coating process. In situ polymerization and low energy polymer grafting can be used in other situations.

In some instances, it may be necessary to coat the substrate with an adhesion primer to improve bondability to the intermediate polymer layer before the substrate is functionalized. Even glass and metal membrane substrates can be functionalized by the process of this invention.

EXAMPLES

Example 1 e-PTFE films were treated with $H_2$ and/or $NH_3$ plasma under varying plasma conditions. The monomer flow rate varied from 40-100 SCCM, reaction pressure varied from 40-100 mtorr, power varied from 5 W-100 W, and time varied from 30 seconds to 6 minutes. The water contact angle of the e-PTFE substrate decreased substantially, but the film in each case lost its mechanical properties making them unusable.

Example 2

A diamond shaped ePTFE film was coated with 0.1 μm thick Parylene C (derived from monochloro p-Xylylene dimer) coating followed by treatment with $NH_3$ plasma at MFR of 73 SCCM, Power 10 W, reaction time 2 minutes. The substrate showed no reduction in tensile properties. The substrate porosity was retained. XPS analysis revealed almost complete absence of F and emergence of approximately 9% N concentration on the surface. Cl from Parylene C and Oxygen from surface oxidation were also visible in the spectrum.

Example 3

An ePTFE tubular substrate was coated with 0.06 μm thick coating of Parylene N (derived from unsubstituted p-Xylylene dimer) followed by treatment with $NH_3$ plasma at MFR of 73 SCCM, power ranging from 2-10 W, reaction time 1-3 min. The modified substrate had a low contact angle of 8 degrees with water and showed no reduction in tensile properties after treatment. XPS analysis of the surface of treated substrate showed presence of significant amount of nitrogen. Biocompatibility studies revealed significant enhancement in the growth of cellular matrix on modified ePTFE substrates compared to the unmodified substrate. Ammonia plasma treated Parylene film also showed good blood compatibility.

Example 4

A microporous polypropylene film (Celgard 2500) was coated with an ultrathin (0.05 μm) film of Parylene N and subsequently treated with $NH_3$ plasma for 5 minutes at an RF power of 5 W. The treatment resulted in drop in Liquid Entry Pressure (LEP) in spite of the resistance offered by the Parylene coating.

Example 5

A commercially procured PEEK membrane (PEEK 100) with a pore size of approximately 0.1 μm was coated with a thin (0.1 μm) coating of Parylene N and subsequently treated with $NH_3$ plasma at MFR of 73 SCCM, power 10 W, reaction time 7 minutes. The treated substrate had a water contact angle of 25 degrees compared to water contact angle of over 90 degrees for the untreated substrate.

Example 6

Several strands of Polypropylene Hollow fiber membrane (X30-240) were coated with a relatively thick (0.3 μm) Parylene N coating and subsequently treated with $NH_3$ plasma at MFR of 73 SCCM, RF power 10 W, reaction time 5 minutes. The treated hollow fiber membrane was tested at an external facility for its effect on the refolding of TGF β3 protein, an important human growth factor. While the bare Parylene N coated hollow fiber led to profuse aggregation, with no significant change in dimer yield compared to the control, the $NH_3$ treated hollow fiber membrane led to lesser aggregation although the dimer yield was not affected. Gas permeability measurements showed that the membrane pores were almost completely blocked after the Parylene coating.

Example 7

Several strands of Polypropylene Hollow fiber membrane (X30-240) were coated with an ultrathin (0.047 μm) Parylene N coating and subsequently treated with $NH_3$ plasma at MFR of 73 SCCM, RF power 10 W, reaction time 3 minutes. The treated hollow fiber membrane was tested at an external facility for its effect on the refolding of TGF (33 protein, an important human growth factor. While both Parylene N coated hollow fiber membrane and $NH_3$ treated hollow fiber membrane lead to aggregation comparable to control, the dimer yield for both hollow fiber membranes were significantly increased. The yield was remarkably high (100% higher) for the $NH_3$ treated hollow fiber membrane compared to 40% increase for only Parylene N coated hollow fiber membrane. No change in the pH of the solution was observed over a period of 48 hours. The experiment confirmed the positive advantage of the open polymer structure as well as N functionality on TGF (33 folding. Permeability experiment confirmed that the pores of the hollow fiber membrane were not affected by the Parylene coating.

Example 8

Several strands of polypropylene hollow fiber membrane (X30-240) were coated with a relatively thick (0.3 μm) Parylene N coating and subsequently treated with $O_2$ plasma at MFR of 100 SCCM, RF power 10 W, reaction time 1 minute. The treated hollow fiber membrane had low water contact angle of approximately 10 degrees after plasma treatment. The treated hollow fiber membrane was tested for its effect on the refolding of TGF (33 protein, an important human growth factor. While the bare Parylene N coated hollow fiber membrane lead to profuse aggregation, with no significant increase in dimer yield compared to the control, the $O_2$ plasma treated hollow fiber membrane, led to significant aggregation in the form of both particulate structures and fibril thread like structures. The pH of the test solution decreased from 9.50 to 9.10 at the end of the experiment.

Example 9

Glass coverslips were coated with Parylene N after priming with a siloxane polymer. The Parylene coated coverslips were subsequently treated with $NH_3$ plasma, $O_2$ Plasma and perfluorohexane plasma in separate experiments to create N, O and F functionality. The treated glass cover slips had a contact angle of 58, 62 and 118 degrees with water when measured at the test site. The treated and untreated coverslips were later evaluated for cell adhesion and spreading using a HeLa cells line after 48 hours. While Parylene N coated, Parylene/$O_2$ plasma treated and Parylene N/HFE treated coverslips showed less affinity for HeLa cells compared to the control, the Parylene N/$NH_3$ treated coverslips showed significant improvement in cell adhesion and spreading. Almost all the cells were able to attach and attain proper morphology showing good health of culture over the aminated Parylene N surface.

Example 10

PTFE microfilter membrane (TF 450, pore size 0.45 um, Gelman Science) was coated on both sides with an ultrathin Parylene N coating. The gas permeability and water contact angle of the coated and uncoated membranes were measured. The membranes were subsequently treated with $NH_3$ plasma at MFR of 73 SCCM, RF Power 5 W, reaction time 3 minutes and tested again. The results are summarized in Table 1. The results confirmed that while there was no significant change in contact angle with water after $NH_3$ plasma treatment of the uncoated PTFE membrane, adding an intermediate ultrathin coating of Parylene N prior to $NH_3$ plasma treatment resulted in a significant decrease in the substrate contact angle with water. The gas permeability characteristic of the membrane remained unaltered.

TABLE 1

| Substrate | Pore size | Contact Angle with Water before treatment (upper side/ lower side) | Thickness of Parylene N | N2gas Permeability before and after Parylene Coating cm3/cm2 · sec · psi | Contact angle After NH3 Plasma (upper side/ lower side) |
|---|---|---|---|---|---|
| TF 450 | 0.45 μm | 126/140 | — | 5.88 | 121/139 |
| TF 450 | 0.45 μm | 126/140 | 0.0356 μm | 5.95 | 30/0 |

Example 11

Whatman Anodisc Inorganic filter membrane (pore size 0.02 um) were coated with an ultrathin Parylene N coating. The gas permeability and water contact angle of the coated and uncoated membranes were measured. The membranes were subsequently treated with $CF_4$ plasma at MFR of 44.5 SCCM, RF Power 25 W, reaction time 2 minutes and tested again. The results are summarized in Table 2. The results confirmed that while the Inorganic filter membrane without the intermediate Parylene N coating remained wettable after the $CF_4$ plasma treatment, adding the ultrathin intermediate layer of Parylene N resulted in substantial increase in the contact angle of the substrate with water. This indicated that the intermediate layer provided a functionalizable surface without any change in the gas permeability of the membrane.

TABLE 2

| Substrate | Pore size | Contact Angle with Water before treatment (upper side/ lower side) | Thickness of Parylene N | N2gas Permeability after Parylene Coating cm3/cm2 · sec · psi | Contact angle After $CF_4$ Plasma treatment (upper side/ lower side) |
|---|---|---|---|---|---|
| Anodisc-47 | 0.02 μm | 14/47 | — | 0.65 | 14/17 |
| Anodisc-47 | 0.02 μm | 14/47 | 0.0356 μm | 0.64 | 122/139 |

The processes and substrates discussed above are exemplary only. The novel concept of modifying the substrate with a Parylene treatment before functionalization can find revolutionary application in biomedical and biochemical engineering, water purification, electro chemistry, gas filtration, molecular separation, food industry and others. It is contemplated that the present invention may be carried out through means other than that specifically described herein.

The invention claimed is:

1. A method for modifying a surface of a porous substrate, the method comprising:
   depositing a polymer coating onto the surface at ambient temperature to a thickness of less than 0.1 μm to form a coated porous substrate, wherein the polymer coating comprises poly (p-xylylene) or a derivative thereof, and wherein the polymer penetrates into pores of the porous substrate but does not substantially alter porosity of the porous substrate, wherein the porous substrate lacks a primary or secondary aliphatic hydrogen atom; and
   exposing the coated porous substrate to a plasma environment having a radio frequency (RF) power of less than or equal to 10 watts, and a monomer at a monomer flow rate of at least 40 standard cubic centimeters per minute (SCCM) to chemically bond a functional agent to the coated porous substrate.

2. The method as in claim 1 wherein the porous substrate is selected from the group consisting of polytetrafluoroethylene, expanded-polytetrafluoroethylene, sintered-polytetrafluoroethylene, electrospun-polytetrafluoroethylene, polyether ether ketone, polyvinyl difluoride, polyamide, polyimide, polyether sulfone, and ceramics.

3. The method as in claim 2 wherein the porous substrate has a maximum pore diameter of less than 100 μm.

4. The method as in claim 3 wherein the porous substrate has a maximum pore diameter of less than 1 μm.

5. The method as in claim 4 wherein the porous substrate has a maximum pore diameter of less than 100 nm.

6. The method as in claim 1, including depositing the polymer coating on the porous surface in the absence of a solvent.

7. The method as in claim 6, including depositing the polymer coating on the porous surface in an environment of less than 101 kPa.

8. The method as in claim 1 wherein the functional agent is an atom of or molecule containing one or more of nitrogen and, fluorine.

9. The method as in claim 1 wherein the porous substrate is hydrophobic, and the functional agent is hydrophilic.

10. The method as in claim 1 wherein the porous substrate is hydrophilic, and the functional agent is hydrophobic.

11. The method as in claim 1 wherein the monomer is ammonia.

12. The method as in claim 11 wherein an exposure time of the coated porous substrate to the plasma environment is less than 10 minutes.

13. A substrate, comprising:
   a porous body having first and second opposed surfaces and comprising a material lacking a primary or secondary aliphatic hydrogen atom;
   a polymer coating on at least one of the first and second surfaces, the polymer coating comprising poly (p-xylylene) or a derivative thereof and having a thickness of less than 0.1 μm; and a functional agent chemically bonded by a plasma treatment to the polymer coating, wherein the functional agent includes an atom of or a molecule containing nitrogen.

14. The substrate as in claim 13 wherein the substrate is a separation membrane.

15. The substrate as in claim 14 wherein the substrate has a maximum pore size of less than 1 µm, and wherein the polymer coating penetrates into pores of the porous substrate but does not substantially alter porosity of the porous substrate.

* * * * *

UNITED STATES PATENT AND TRADEMARK OFFICE
CERTIFICATE OF CORRECTION

PATENT NO. : 12,227,728 B2
APPLICATION NO. : 17/158651
DATED : February 18, 2025
INVENTOR(S) : Ashok Sharma It is certified that error appears in the above-identified patent and that said Letters Patent is hereby corrected as shown below:

In the Specification

Column 10, Line 2, "an external facility for its effect on refolding of TGF (33" should read -- an external facility for its effect on refolding of TGF β3 --, Column 10, Line 13, "structure as well as N functionality on TGF (33 folding" should read -- structure as well as N functionality on TGF β3 --, Column 10, Line 27, "its effect on the refolding of TGF (33 protein, an important" should read -- its effect on the refolding of TGF β3 protein, an important --.

Signed and Sealed this
Thirteenth Day of May, 2025

Coke Morgan Stewart
*Acting Director of the United States Patent and Trademark Office*